United States Patent
Logothetis et al.

[11] Patent Number: 5,942,674
[45] Date of Patent: Aug. 24, 1999

[54] METHOD FOR DETECTING OXYGEN PARTIAL PRESSURE USING A PHASE-TRANSFORMATION SENSOR

[75] Inventors: Eleftherios Miltiadis Logothetis, Birmingham; Richard E. Soltis, Saline, both of Mich.

[73] Assignee: Ford Global Technologies, Inc., Dearborn, Mich.

[21] Appl. No.: 08/906,237

[22] Filed: Aug. 4, 1997

[51] Int. Cl.[6] .......................... G01N 27/12; G01N 27/46
[52] U.S. Cl. ...................... 73/23.32; 73/29.01; 73/31.01; 73/31.05; 422/83; 422/90; 436/137
[58] Field of Search ................ 73/23.32, 32.31, 73/31.01, 31.05, 31.06, 29.01; 422/83, 90, 94, 98; 436/137

[56] References Cited

U.S. PATENT DOCUMENTS

| | | | |
|---|---|---|---|
| 3,933,028 | 1/1976 | Laud et al. ................................ 73/23 |
| 4,208,265 | 6/1980 | Hori et al. ........................... 204/195 S |
| 4,209,378 | 6/1980 | Schinohara et al. ..................... 204/195 |
| 4,228,128 | 10/1980 | Esper et al. ............................... 422/98 |
| 4,253,931 | 3/1981 | Gold et al. ......................... 204/192 SP |
| 4,320,378 | 3/1982 | Taniguchi et al. ......................... 338/34 |
| 4,328,295 | 5/1982 | Tanaka et al. ............................ 429/193 |
| 4,328,296 | 5/1982 | Tanaka et al. ............................ 429/193 |
| 4,351,182 | 9/1982 | Schmidberger .......................... 73/27 R |
| 4,535,316 | 8/1985 | Wertheimer et al. ..................... 338/34 |
| 4,574,264 | 3/1986 | Takahashi et al. ........................ 338/34 |
| 4,764,343 | 8/1988 | Nyberg ....................................... 422/83 |
| 4,824,549 | 4/1989 | Hamada et al. ......................... 204/410 |
| 5,017,340 | 5/1991 | Pribat et al. ............................... 422/98 |
| 5,238,549 | 8/1993 | Makino et al. ........................... 204/425 |

(List continued on next page.)

OTHER PUBLICATIONS

E. M. Logothetis, "$ZrO_2$ oxygen sensors in automotive applications," 1981, The American Ceramic Society.

E. M. Logothetis, "Resistive-Type Exhaust Gas Sensors," American Ceramic Society.

E. M. Logothetis, "Air-to-Fuel Sensors Based on Oxygen Pumping" 1987, pp. 1058–1073, Reprinted from the Ceramic Engineering and Science Proceedings, vol. 8, No. 9–10.

G. L. Beaudoin, K. R. Laud, E. M. Logothetis, A. H. Meitzler, and K. Park, "CoO Sensors for Measurement and Control of Exhaust from Lean–Burn Engines," 760312, Engineering & Research Staff, Ford Motor Company.

Kwansuh Park and E. M. Logothetis, "Oxygen Sensing with $Co_{1-x}Mg_xO$ Ceramics," 1977, p. 1443–1446, Reprinted from Journal of the Electrochemical Society, vol. 124, No. 9.

Michael L. Post, Brian W. Sanders and P. Kennepohl, "Thin film of non–stoichiometric perovskites as potential oxygen sensors," 1993, pp. 272–275, Sensors and Actuators B, 13–14.

*Primary Examiner*—Hezron Williams
*Assistant Examiner*—J. David Wiggins
*Attorney, Agent, or Firm*—Lorraine S. Melotik

[57] ABSTRACT

The invention is a sensing method and an oxygen sensor for detecting a change of oxygen partial pressure in an ambient atmosphere through a change of a measurable physical property of a sensing material. The sensor includes a sensing material selected from metal or its oxides which, when at an elevated temperature and exposed to a gas containing a changing partial pressures of oxygen, is capable of changing from one metal or metal oxide phase to another such oxide phase and vice versa. Associated with such phase change is a change in a measurable physical property of the material. The sensor also includes heating means, connectable to a power source, maintaining a temperature gradient across the sensing material since it is critical that the sensing material exist in at least two phases during active sensing. An output signal is furnished in response to the change in a physical property, like electrical resistance, of a portion of or of the entire material in response to change in oxygen partial pressure.

18 Claims, 3 Drawing Sheets

U.S. PATENT DOCUMENTS

| | | | |
|---|---|---|---|
| 5,306,700 | 4/1994 | Hojaji | 505/450 |
| 5,372,838 | 12/1994 | Aoki et al. | 427/58 |
| 5,384,030 | 1/1995 | Duce et al. | 204/426 |
| 5,397,541 | 3/1995 | Post | 422/98 |
| 5,417,061 | 5/1995 | Maeda et al. | 60/277 |
| 5,443,711 | 8/1995 | Kojima et al. | 204/429 |
| 5,480,535 | 1/1996 | Kondo et al. | 204/425 |
| 5,492,612 | 2/1996 | Kennard, III et al. | 204/429 |
| 5,492,886 | 2/1996 | Morris | 505/482 |
| 5,510,013 | 4/1996 | Hippe et al. | 204/426 |
| 5,520,787 | 5/1996 | Hanagan et al. | 204/409 |
| 5,538,612 | 7/1996 | Kojima et al. | 204/429 |
| 5,734,091 | 3/1998 | Kudo et al. | 73/23.2 |
| 5,783,153 | 7/1998 | Logothetis et al. | 422/83 |

METHOD FOR DETECTING OXYGEN PARTIAL PRESSURE USING A PHASE-TRANSFORMATION SENSOR

Reference is made to related U.S. application Ser. No. 08/905,372, now U.S. Pat. No. 5,783,153 dated Jul. 21, 1998, titled "Metal Oxide Oxygen Sensors Based on Phase Transformation" concurrently filed with this application and having the same inventorship.

FIELD OF THE INVENTION

This invention is directed to oxygen sensors which detect changes in oxygen partial pressure in an ambient atmosphere based on phase changes of a material like cobalt oxide, e.g., from one phase of cobalt oxide ($Co_3O_4$) to another (CoO).

BACKGROUND OF THE INVENTION

Oxygen sensors have received widespread attention particularly for applications like combustion control, process control, and medical applications. In the automotive area, oxygen sensors are used to control the Air-to-Fuel Ratio (A/F) of internal combustion engines. The great majority of present day automobiles employ an electrochemical-type oxygen sensor to control the A/F ratio. Generally this ratio is controlled at the stoichiometric value, about 14.4–14.7, where the so-called three-way catalysts have the greatest efficiency for eliminating regulated emissions (hydrocarbons, carbon monoxide, and oxides of nitrogen) from the exhaust gas. The automotive oxygen sensor, sometimes called a lambda sensor, includes an oxygen-ion-conducting solid electrolyte, generally $ZrO_2$, in the form of a thimble with porous platinum electrodes deposited on the outside and the inside surfaces of the thimble. The inside of the thimble is exposed to ambient air as a reference atmosphere, whereas the outside of the thimble is exposed to the exhaust gas. When the thimble is heated (e.g. temperatures higher than 300° C.) and there is a difference in the oxygen partial pressures $P_{O2}$ between the two sides of the $ZrO_2$ thimble, an electromotive force (emf) is generated between the two Pt electrodes with a value given by the Nernst equation: emf=(RT/kT) ln($P_{O2}$,exh/$PO_2$,air).

Figure 1:
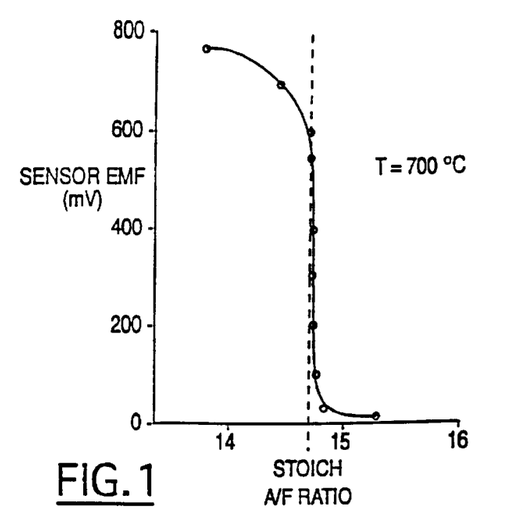
FIG. 1 is a graph showing the measured emf of a conventional automotive $ZrO_2$ oxygen sensor (lambda sensor) as a function of the Air-to-Fuel Ratio of an engine.

When the sensor is placed in the exhaust gas of a vehicle, and the A/F is varied, the sensor emf shows a large and abrupt change at the stoichiometric A/F value as shown in FIG. 1. The reason is that the thermodynamic equilibrium oxygen partial pressure in the exhaust gas changes by many orders of magnitude at the stoichiometric A/F ratio. Away from stoichiometry, the emf varies only slowly with A/F because the partial oxygen pressure also changes only slowly with A/F.

Another type of a high temperature oxygen sensor useful in automotive applications is a resistive-type sensor based on $TiO_2$. At elevated temperatures, the electrical resistivity of $TiO_2$ and of many other metal oxides such as $SrTiO_3$ and CoO depends on the oxygen partial pressure $P_{O2}$ in the ambient gas atmosphere. This dependence is generally weak, e.g. for $TiO_3$, $SrTiO_3$ and CoO this dependence is a positive or negative ¼ to ⅙ power dependence. In spite of their weak $P_{O2}$ sensitivity, $TiO_2$ sensors are useful for stoichiometric A/F control because they also exhibit a large and abrupt resistance change at the stoichiometric A/F value as the result of the large change in exhaust gas $P_{O2}$ near stoichiometry.

Figure 3:
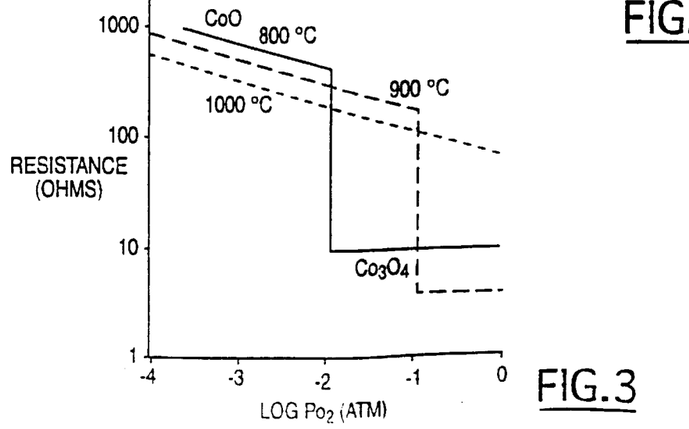
FIG. 3 is a graph showing the stepwise change in resistance of a cobalt oxide ceramic sample as a function of $P_{O2}$ at several temperatures due to the phase change from CoO to $Co_3O_4$.

FIG. 3 shows results of measurements of the resistance of a porous cobalt oxide ceramic as a function of $P_{O2}$ at several temperatures. The large stepwise change in the resistance of the sample at temperatures below 1000° C. is associated with the phase change from CoO to $Co_3O_4$. The resistivity of $Co_3O_4$ is independent of $P_{O2}$, whereas the resistivity of CoO decreases with increasing $P_{O2}$ according to the relationship R=A exp(E/kT) $(P_{O2})^{-¼}$. This property of CoO has been utilized in fabricating oxygen sensors as disclosed by G. L. Beaudoin et al., SAE Paper #760312, Feb. 23, 1976 and U.S. Pat. No. 3,933,028 to K. R. Laud et al. The oxygen sensitivity of this sensor is, however, low.

There is a growing need for oxygen sensors that can measure A/F away from stoichiometry, in particular in the lean A/F region where excess oxygen is employed. These A/F ratios are often 19–40. Many engines are being modified for lean operation because of the fuel economy advantages which can be achieved. These sensors must have high $P_{O2}$ sensitivity because the oxygen partial pressure in the exhaust gas does not change appreciably with A/F in this region. The $ZrO_2$ lambda sensor and the resistive-type sensors mentioned above, have very limited sensing ability away from stoichiometry. In addition the resistive-type sensor generally have a strong dependence on temperature.

Figures 4, 6:
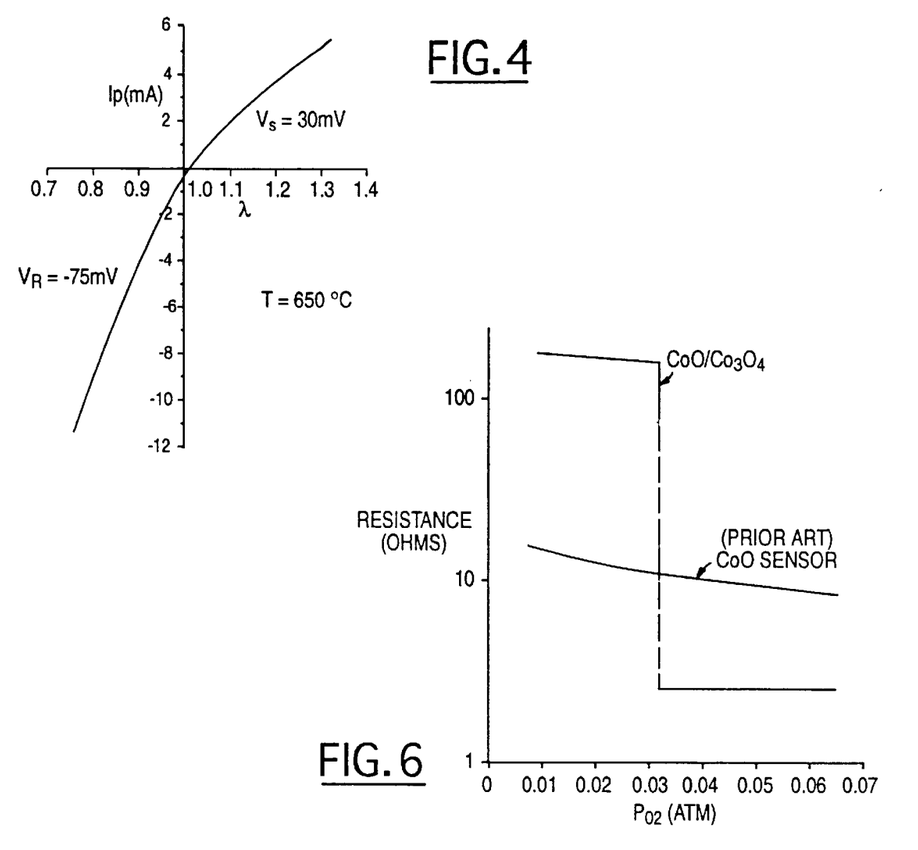
FIG. 4 is graph showing the pumping current of a UEGO sensor as a function of lambda.
FIG. 6 is a graph showing the resistance (ohms) response of a $CoO/Co_3O_4$ limit-cycle type sensor according to an embodiment of a copending application to varying $P_{O2}$. The response of a prior art CoO sensor is also shown for comparison.

On the other hand, another type of sensor, i.e., $ZrO_2$ based sensors operating in the oxygen pumping mode have much higher sensitivity (e.g. 1st-power $P_{O2}$ dependence) away from stoichiometry. Examples of this type of sensor are the Universal Exhaust Gas Oxygen Sensor (UEGO) and the Lean Exhaust Gas Oxygen Sensor (LEGO) based on two $ZrO_2$ cells. FIG. 4 shows the output of the UEGO sensor as a function of $\lambda$=(A/F)/(A/F)$_{stoic}$, the A/F normalized to the stoichiometric A/F value, (A/F)$_{stoic}$. These sensors are complex, however, and consequently expensive to manufacture which Limits their widespread commercialization. Consequently, effort has been expended to develop a simple sensor having high oxygen sensitivity for A/F measurement away from stoichiometry.

Figure 2:
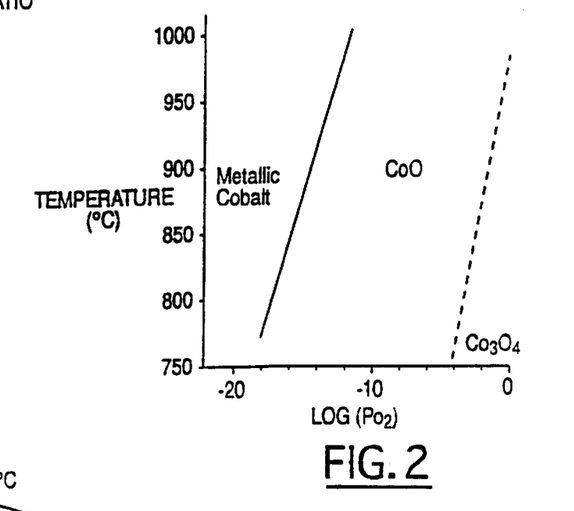
FIG. 2 is a $P_{O2}$ v. T graph of the phase diagram for the Co—O system.
Figure 5:
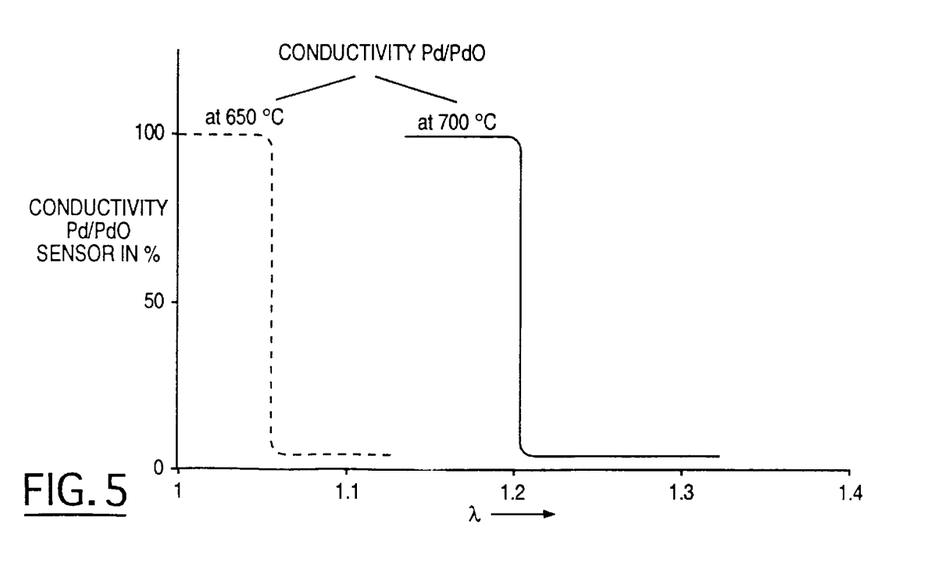
FIG. 5 is a graph showing the response of a prior art Pd/PdO sensor.

Another type of sensor for monitoring the oxygen content in oxygen rich exhaust gases from furnaces is disclosed in U.S. Pat. No. 4,351,182 to Schmidberger. The oxygen sensitive element is a palladium layer maintained at a specific high temperature, e.g., 700° C., whereby the palladium metal (Pd) changes phase to palladium oxide (PdO) when the oxygen partial pressure exceeds a specific "critical" value, $P_{O2,c}$. It is disclosed that the phase change from Pd to PdO and vice versa causes a change in the electrical conductivity by a factor of about 20 which is used to provide a sensor output signal. This is shown in FIG. 5 where the percent change in the conductivity of Pd/PdO is plotted as a function of the $\lambda$ for two different temperatures. It is also known that many metal oxides change to other metal oxide phases when the temperature or the $P_{O2}$ are changed appropriately. For example, at a given temperature, CoO is stable at low $P_{O2}$, but at higher $P_{O2}$, it transforms to $Co_3O_4$ as shown in FIG. 2. Such metal-oxide to metal-oxide phase transitions are also generally accompanied by large changes in electrical resistivity as shown in FIG. 3 for cobalt oxide. Similarly, another physical property, optical absorption, in the case of phase transformations for Sr-Fe-oxide, shows a large associated change.

Such phase transitions, however, are known to be generally accompanied by significant hysteresis unless the $P_{O2}$ is changed to a value substantially larger (or smaller) than $P_{O2,c}$. Hysteresis is related to the time that it takes for the material to change from one phase to another and is believed to be associated with a necessary nucleation process, i.e., formation of critical size nuclei of the new phase. The presence of hysteresis in phase transformation type sensors would negatively impact their usefulness since they would have relatively long response time. In copending application entitled "Metal Oxide Oxygen Sensors Based on Phase Transformations" mentioned above, we disclose oxygen sensors based on such phase changes with do not suffer from the problems associated with nucleation processes. These sensors generally comprise sensing material across which is provided a temperature gradient to maintain the sensing material in at least two phases with a boundary line therebetween. The movement of the boundary line across a fixed detecting location on the material is used to indicate a change in oxygen partial pressure of the ambient atmosphere to which the sensor is exposed.

Oxygen or A/F sensors which exhibit a relatively abrupt and large change in output, e.g., related to change in resistivity of the material, at some specific "critical" value of the oxygen partial pressure $P_{O2,c}$ or $(A/F)_c$ can conveniently provide information only on whether the ambient $PC_{O2}$ (or A/F) is lower or higher than $P_{O2,c}$ or $(A/F)_c$. When these sensors are used to feedback control the ambient $P_{O2}$ or (A/F) at some specific value $P_{O2,c}$ or $(A/F)_c$, the feedback control is of the "limit-cycle" type rather than proportional control. For example, in the limit-cycle control of A/F of an engine, the A/F ratio is ramped from a value lower than $(A/F)_c$ to a value higher than $(A/F)_c$ or vice versa, with the direction of the ramping depending on the sensor output. When A/F passes through $(A/F)_c$, the sensor signal changes from a low to a high value or from a high to a low value and the electronic feedback system is ordered to change direction of the A/F sweep. Consequently, the A/F oscillates between two A/F values, one lower and the other higher than $(A/F)_c$, at a certain frequency called "limit-cycle frequency". This is the basic method by which the $ZrO_2$ lambda sensor is used extensively for stoichiometric A/F control of present day vehicles and such limit-cycle control is the principle of sensing and controlling of the copending application invention mentioned above.

However, it has been found that a proportional A/F control rather than a limit-cycle control can lead to better performance of vehicles with respect to tailpipe emissions. In this respect, the more complex and costly $O_2$-pumping-based $ZrO_2$ sensors (e.g., the UEGC sensor) with their approximately linear response to A/F ratio are preferred over the Nernst-type $ZrO_2$ lambda sensor for stoichiometric A/F control. The same $O_2$-pumping-based A/F sensors can also be used for proportional A/F control away from stoichiometry, e.g., in the lean.

The simpler and less expensive resistive-type sensors of the prior art such as the CoO sensor are applicable for proportional A/F control in the lean, but their accuracy is limited because of their low $P_{O2}$ sensitivity, as discussed previously. The more sensitive resistive sensors of the prior art with a sharp and abrupt change in their response at some lean A/F value (e.g., the Pd/PdO sensor of U.S. Pat. No. 4,351,182) obviously cannot be used for proportional control. The sensor of noted copending application "Metal Oxide Oxygen Sensors Based on Phase Transformations" also shows a relatively abrupt and large change in output, e.g., related to the electrical resistance change of the sensing material at some specific value of the oxygen partial pressure of A/F, and hence can not be used for proportional control. The response of the sensor is shown in FIG. 6. In this example the sensor is designed to detect a $P_{O2}$ of 0.031 atm. For comparison, the response of the prior art CoO resistive sensor is also shown in FIG. 6.

Because of the disadvantages of the $O_2$-pumping-based electrochemical $Zr_{O2}$, it is still highly desirable to develop A/F sensors, e.g. resistive-type sensors which have a non-abrupt response but also are very sensitive, especially in the lean A/F region. This is an object of the present invention oxygen sensor. The present invention overcomes the deficiencies of prior art sensors and provides an oxygen sensor useful for automotive applications having excellent sensitivity and response time in a variety of A/F ratios, including that of lean-burn gasoline or diesel engines.

SUMMARY OF THE INVENTION

The invention is an oxygen sensor for detecting a change of oxygen partial pressure in an ambient atmosphere. More particularly, the sensor comprises a sensing material being selected from metal or its oxides and which, when at an elevated temperature and exposed to a gas containing a changing partial pressures of oxygen, is capable of changing from one metal or metal oxide phase to another such oxide phase and vice versa and associated therewith a change in a measurable physical property thereof. The sensor also includes heating means connectable to a power source able for maintaining a temperature gradient across the sensing material whereby said material exists, during active sensing operation, in at least two of the phases defining a boundary line therebetween generally perpendicular to the longitudinal axis of the temperature gradient. Further the sensor includes means for furnishing an output signal in response to the change in a physical property of the sensing material, the property being measured across a portion or all of the sensing material which includes, during active sensing operation, at least two of the phases. Preferably, the physical property is selected from the group consisting of electrical resistance, mass, and optical absorption.

In another embodiment, the present invention is a method for detecting a change of oxygen partial pressure in an ambient atmosphere through a change of a measurable physical property of a sensing material. This method includes the steps of locating a sensor in contact with an ambient atmosphere containing oxygen. The sensor comprises a sensing material described above which is, during active sensing operation, capable of being present in at least two phases defining a boundary line therebetween, the phases being selected from metal and oxides thereof. As would be appreciated, at least one of the phases hence is an oxide phase as defined above. The method further comprises the steps of maintaining a temperature gradient across the sensing material so as to maintain the material in at least two phases defining a boundary line therebetween generally perpendicular to the longitudinal axis of said temperature gradient, and furnishing an output signal in response to a change in the physical property of the sensing material, the property being measured across a portion or all of the sensing material which includes, during active sensing operation, at least two of the phases.

Preferably, the step of furnishing an output signal includes measuring the electric resistance of the material by spaced apart electrical means encompassing therebetween the sensing material portion. For example, if the sensing material is a rectangular layer, these means would optimally be located along the length of two opposing sides of the sensing material layer so that the means are generally either perpendicular to or parallel to the axis of the temperature gradient of the layer. They may be located on the surface of or within the layer or the bulk of the sensing material, generally placement on the surface being more practical.

The oxygen sensor of the present invention advantageously provides a relatively low cost sensor with excellent sensitivity and response time. In addition, the sensor is much less complex to fabricate than present sensors, e.g., because it does not need a high quality seal between exhaust gas and air as employed in many conventional sensors.

DETAILED DESCRIPTION OF PREFERRED EMBODIMENTS

The oxygen sensor disclosed herein is useful for detecting a change of oxygen partial pressure in an ambient atmosphere. It includes a sensing material selected from metal or its oxides which, when at an elevated temperature and exposed to a gas containing a changing partial pressure of oxygen, is capable of changing from one metal or metal oxide phase to another such oxide phase and vice versa. This gas may be for example automotive vehicle exhaust gas as from gasoline or diesel engines. Associated with such phase changes is a change in a measurable physical property of the material, like electrical resistance. Thus, the sensing material undergoes a change in a measurable physical property in response to a change in the oxygen partial pressure to which the sensing material is exposed during sensing operation.

The sensing material may be a single metal, oxide thereof, or a compound of two or more metals or oxides thereof. It may also be a mixture of such materials. Preferred metals include, but are not limited to, metals like copper, palladium, indium, ruthenium, and rhodium; 3d transition metals; and rare earth elements. Exemplary of such 3d transition metals are titanium, vanadium, chromium, manganese, iron, cobalt, and nickel to name a few. Exemplary rare earth elements include La, Ce, Pr, Nd, Sm, Eu, Gd, Er etc. The sensing material may be a ternary and higher order compounds of the above metals with other elements like alkaline earth elements, e.g., calcium, strontium, or magnesium or oxides thereof such as CoMgO and SrFeO, or such compounds formed with rare earth elements such as $La_2CuO_3$, $La_2CuO_3$, $PrFeO_3$. Still other ternary and higher order compounds or oxides thereof of rare earth elements with other elements, e.g., $Y_mBa_nCu_kO_x$ may also be employed herein. Mixtures of any of these materials would also be useful. The sensing materials useful in this invention are not limited to those listed above but may be any metal material or oxide thereof which undergoes a phase change in response to changing partial oxygen pressures and has associated therewith a change in a measurable physical property.

The material may be present in bulk form or as a layer on a substrate, and the substrate may be planar. The substrate may be selected from any suitable material which will be dependent on the particular application of the sensor as will be described in further detail below.

As an example, the sensing material may be cobalt, which can convert to cobalt oxide (CoO or $Co_3O_4$) depending on the temperature and partial pressure of the oxygen. That is, as seen in FIG. 2, the particular phase of the material depends on the temperature and partial oxygen pressure to which the material is exposed. FIG. 2 shows a part of the $P_{O2}$-T phase diagram for this system. The solid and the dotted lines separate the Co, CoO, and $Co_3O_4$ phases. For (T, $P_{O2}$) pairs corresponding to the left of the solid line, the sensing material exists only as metallic cobalt. Between the solid and the dotted lines, the material exists as CoO; whereas, to the right of the dotted line, the material exists only as $Co_3O_4$ On the solid and dotted lines the material is a mixture of the two adjacent phases.

We have found that it is critical to the present invention that the sensor also includes a heating means, connectable to a power source, for maintaining a temperature gradient across the sensing material during its operation. As disclosed above, during the active sensing operation, according to the present invention, because a temperature gradient is applied across the sensing material it exists in at least two of its phases (FIG. 7, phases A and B), one of which will be an oxide phase, defining a boundary line 22 therebetween. When these phases form, the boundary line therebetween will be located generally (approximately) perpendicular to the axis of the temperature gradient. The exact shape of the boundary line, i.e., the need to be a straight line, and its perpendicular relationship to the temperature gradient axis is not critical to the functioning of this invention sensor. Hence, this temperature gradient maintains the presence of at least two different phases, which may be, e.g., cobalt metal and CoO or two forms of cobalt oxide during active sensing operation. The material may exist in more than two separate phases during operation, for example the phases which could exist concurrently could be $Co/CoO/Co_3O_4$, with boundary lines between adjacent two phases. It is to be understood in this invention, that these phases exist at different places in the material, not as homogeneous mixtures thereof, with contact between the phases being only at the boundary line between phases. That is, the FIG. 7 sensor embodiment shows two phases as A and B with the boundary line 22 therebetween. These phases A and B are kept separate from one another by means of the use of the heating means which critically maintains a temperature gradient across the material. By maintaining these at least two phases, the measured physical property across the material, e.g., electrical resistance, displays a gradual change rather than the abrupt step change of limit-type sensors with changing partial oxygen pressure. This allows the present invention sensor to provide, e.g., proportional A/F control for automotive vehicles, gasoline or diesel, rather than a limit-cycle type function.

As discussed above, when materials such as cobalt oxide change from one phase to another phase, there is an associated hysteresis effect. In operation, it may be desirable to expose the sensor comprised of a metal like cobalt to oxygen to initiate formation of an oxide phase or phases prior to actual operation of the sensor, i.e., to pre-condition the sensor, e.g., prior to insertion in an automotive exhaust gas system as described in more detail below. This may be done, e.g., by exposing the sensor material to a temperature distribution in the range of 700°–1000° C. in air.

Figure 7:
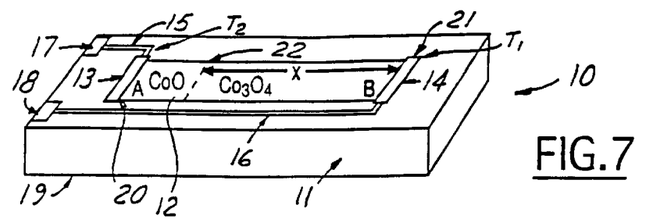
FIG. 7 is an oxygen sensor according to an embodiment of the present invention where the measured physical property of the sensing material is its electrical resistivity.

The sensor also includes a means for furnishing an output signal in response to changes in a physical property of the sensing material measured or detected across a portion or all of the sensing material, which property varies with changes in the oxygen partial pressure of the ambient atmosphere as correlated to phase formation. That area of the material whose physical property is being measured, whether it be a portion or the entire sensing material, is required during active sensing operation to contain at least two phases of the material. Exemplary of these measurable physical properties are electrical resistivity, optical absorption, and mass. One approach concerns measuring the changing electrical resistivity of the portion of the sensing material as it changes with varying oxygen partial pressure. This may involve spaced apart electrical means affixed within or to surfaces of the sensing material. For a rectangular layer as shown in FIG. 7, the electrical means are generally perpendicular to or parallel to the axis of the temperature gradient. These electrical means, which will be discussed further below with respect to the FIG. 7, are able to furnish an output signal in response to the change in the physical property correlated with the phase change of the portion of the sensing material between the electrical means. This portion may vary in size as discussed above necessarily encompassing during active sensing operation at least two phases of the sensing material.

The preferred embodiments of the invention and its method of operation can be further described by reference to the figures. FIG. 7 shows an embodiment of the oxygen sensor 10 which is based on electrical resistance measurement according to the present invention. A layer 12 of the metal (e.g. Co) or the metal oxide (e.g. CoO) is deposited on substrate 11. If resistance is the property being monitored, then the substrate must be electrically insulating. Substrate 11 can be one of many materials known in the art such as alumina, silica, sapphire, and silicon nitride. Still others will be apparent in view of the present disclosure. Layer 12 can be deposited by one of many methods known in the art such as sputtering, electron-beam evaporation, laser ablation, chemical vapor deposition, sol-gel techniques, and thick film printing. Generally, this layer would preferably only be a few microns thick. Thin layers minimize sensor response time limitations arising from the need of $P_{O2}$-related lattice defects in the material (e.g., Co ions in CoO, or O vacancies in $TiO_2$) to diffuse throughout the entire layer. On the other hand, thick layers tend to increase the longevity of the sensors. The sensing material of the present invention preferably has a density which is at least 60% of theoretical density. If the layer is relatively thin (a few microns or less), 100% density is acceptable. If the layer is thick (e.g., several tens of microns or more) substantial porosity and small grain size (e.g., a few microns) are generally needed in order to decrease the distance over which the ions need to diffuse and thus to decrease the sensor response.

In the embodiment of FIG. 7, two electrical contacts 13 and 14 for resistance measurement are deposited on the two ends of material layer 12. Electrical leads 15 and 16 are also deposited on the substrate 11 to connect contacts 13 and 14 to the electrical pads 17 and 18 where a voltage or a current is connected from an external source for the resistance measurement. Electrical contacts, leads and pads are generally made from a high temperature conductor such as platinum.

Further in this embodiment, an electrical heater 19, made for example of platinum, is deposited on the back side of substrate 11 to raise the temperature of sensor 10 to the desired values. Heater 19 is constructed in such a way that it delivers different electrical power to different parts of the substrate so that a temperature gradient is established along the length of sensing material layer 12. The critically of maintaining a temperature gradient across the sensing material has been discussed in detail previously herein. Consequently, the temperature $T_2$ at one end 20 of the sensing material layer is higher than the temperature $T_1$ at the other end 21 of layer 12.

The type and magnitude of the temperature gradient in the sensor 10 depends on the application. In general, the smaller is the T-gradient, the higher is the accuracy of the sensor. If the T-gradient is constant along the sensing material layer 12, a smaller T-gradient means that the difference between $T_1$ and $T_2$ is smaller. In that case, the range of allowable variation of $P_{O2}$ that preserves both phases in the layer is smaller. A typical $P_{O2}$ range is one that covers an order of magnitude, that is the ratio of the maximum and minimum $P_{O2}$ is 10. The temperatures $T_1$ and $T_2$ at the two ends of layer 12 corresponding to these maximum and minimum $P_{O2}$ can be determined from the T-$P_{O2}$ phase diagram (e.g. FIG. 2 for Co—O system). A high accuracy combined with a wide range of $P_{O2}$ measurement may be achieved by generating a special non-constant T-gradient along sensing material layer 12. For example, the heater and the structure can be designed so that the T-gradient is small near the center of layer 12 and very large at the two ends of layer 12.

During the operation of sensor 10 for measuring partial oxygen pressures in the range from a lower value $P_{O2,l}$ to a higher value $P_{O2,h}$, the power to heater 19 is adjusted so that the temperatures $T_1$ and $T_2$ at the two ends 21 and 20 of layer 12 are correspondingly lower and higher than the temperatures which correspond to the transition from one oxide phase to the other at the two oxygen partial pressures $P_{O2,l}$ and $P_{O2,h}$, l=low and h=high. When the $P_{O2}$ in the ambient is within the above range of values, layer 12 contains two sections A and B, each one having one of the two metal oxide phases (e.g., CoO and $Co_3O_4$), with the boundary line 22 between the two phases perpendicular to the axis of the temperature gradient (or in this embodiment, perpendicular to the longitudinal axis of layer 12).

Figure 8:
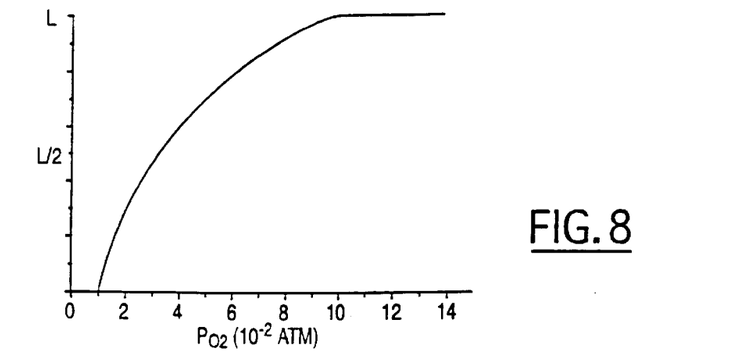
FIG. 8 is a graph which shows the length of the $Co_3O_4$ segment as a function of $P_{O2}$ for an embodiment oxygen sensor according to the present invention.
Figure 9:
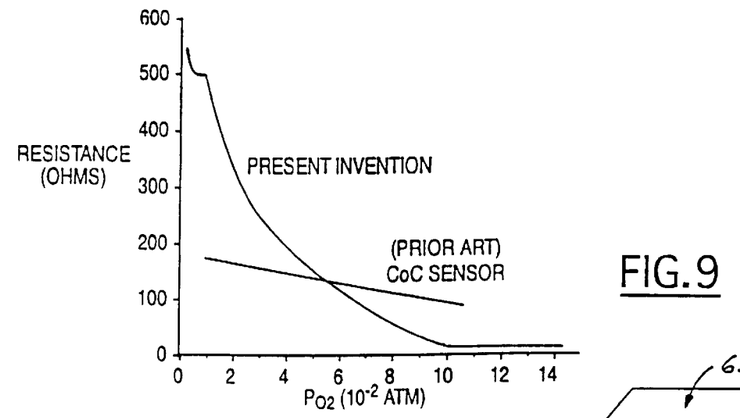
FIG. 9 is a graph showing the electrical resistance of the FIG. 7 sensor as a function of $P_{O2}$ or $O_2$ concentration. The resistance response of a prior art CoO sensor is also shown for comparison.

The electrical resistance between contacts 13 and 14 is obviously the series combination of the resistance of the CoO segment and the resistance of the $Co_3O_4$ segment of the sensing material. As $P_{O2}$ is increased from $P_{O2,l}$ to $P_{O2,h}$, this resistance decreases continuously from a high to a low value as the phase boundary line moves to the left. As an example, FIGS. 8 and 9 show results for a cobalt oxide layer of length L with a constant temperature gradient along L, and $T_1$=860° C., $T_2$=900° C. corresponding to transformation oxygen concentrations of 1% and 10% respectively, $P_{O2}$=$10^{-1}$ atm and $P_{O2}$=$10^{-2}$ atm. FIG. 8 shows the length x of the $Co_3O_4$ segment as a function of the $O_2$ concentration. For $P_{O2}$=$10^{-2}$ (e.g., 1% $O_2/N_2$), the entire layer 12 is CoO; for $P_{O2}$=$10^{-1}$ (e.g., 10% $O_2/N_2$), the entire layer 12 is $Co_3O_4$. During operation, it may be that the sensing material will be present totally as only one phase, e.g., if the partial pressure changes radically as from lean to rich A/F operation. In the case of cobalt oxide, this would mean that the material would be essentially all CoO. While the sensor would not at that time be able to be in active operation to proportionally measure the oxygen concentration, this is not seen as a drawback to the invention. FIG. 9 shows the resistance of layer 12 as a function of the $O_2$ concentration for the same conditions as in FIG. 8. For comparison, the response of a CoO sensor of the prior art is also shown. It is clear that the output of the sensor of the present invention shows a gradual change with $P_{O2}$ rather than an abrupt change at a specific value $P_{O2,c}$ and has excellent sensitivity, much higher than the sensors of the prior art. The result of FIG. 9 is obtained when, of course, the electrical contacts are located at the two ends, of the cobalt oxide layer so that the change in the electrical resistance of the entire length L of the layer is measured. If instead, each contact is placed L/4 (i.e., ¼ of the length L) from each end of the layer, then only the resistance of the middle half (½) of the layer is measured. In this later case, the sensor output (resistance) changes gradually only when the ambient $P_{O2}$ varies between approximately $2.2 \times 10^{-2}$ atm and $5.3 \times 10^{-2}$ atm. It is clear that the range of $P_{O2}$ over which the sensor shows a gradual response depends on the distance between the two contacts and the temperature difference between the locations of the two contacts. It is pointed out that the shape of the R v. $P_{O2}$ curve of FIG. 9 can be adjusted by changing the type of the T-gradient. For example, a non-constant T-gradient can be employed to give a sensor output which is linear with $P_{O2}$.

Figure 10:
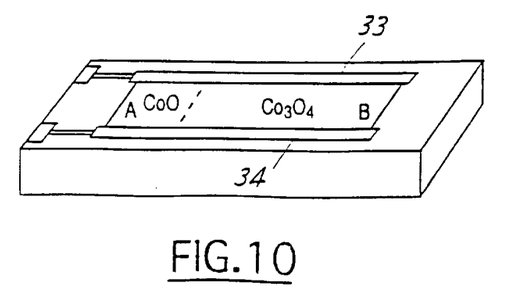
FIG. 10 is a schematic of another embodiment of the present invention sensor which is an electrical resistive type sensor.

FIG. 10 shows another embodiment of the sensor according to the present invention. This differs from that of FIG. 7 in that the resistance measurement contacts 33 and 34 are located on the sides of layer 32 generally parallel to the temperature gradient axis. In this embodiment, the measured resistance is the parallel combination of the resistance of the CoO segment and the $Co_3O_4$ segment.

Figure 11:
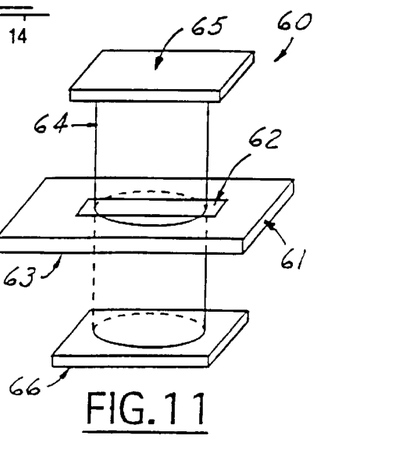
FIG. 11 is a schematic of another embodiment of the present invention sensor where the measured physical property of the sensing material is its optical absorption.

FIG. 11 shows another embodiment 60 according to the present invention where the physical property being measured is optical absorption. Embodiment 60 is similar to embodiment 10 except that electrical leads, pads, and contacts are not needed in embodiment 60. A circular or a rectangular (or other convenient shape) light beam 64 of the proper wavelength from a light source 65 is directed through a portion of the sensing material layer 62 which includes at least two material phases during active sensing. The light transmitted through the sensing material layer 62 and the substrate 61 on which is deposited is detected with a light detector 66. In this embodiment, substrate 61 must be transparent to the light beam 64 but does not have to be electrically insulating. However, if the heating means 63 for providing the temperature gradient across the layer comprises a metal coating, e.g., a discontinuous printed metallic coating as might be used in the prior embodiment, it would still be necessary to provide an electrically insulating substrate. It is also desirable that the heater does not interfere with the optical measurement.

The device of the present invention can be made in planar configurations other than the one shown in FIG. 7. For example, a planar structure can be fabricated similarly to the so-called planar $ZrO_2$ sensors, both the stoichiometric Nernst-type and $O_2$-pumping-based UEGO and LEGO sensors. In this method, a series of ceramic tapes made from $ZrO_2$ (and possibly also from other materials) having appropriate geometry (shape and thickness) together with planar heater and electrodes are pressed together and sintered at high temperatures to form the planar sensor element.

Although planar geometry is a most convenient geometry for establishing a temperature gradient, more 3-dimensional embodiments can also be used. These embodiments as well as others included within the present invention will be apparent to those skilled in the art in view of the present disclosure.

Various preferred embodiments of the invention have now been described in detail. In addition, however, many changes and modifications can be made to these embodiment without departing from the nature and spirit of the invention. Accordingly, it is to be understood that the invention is not limited to these details but is defined by the appended claims.

What is claimed is:

1. A method for detecting a change of oxygen partial pressure in an ambient atmosphere containing oxygen, said method comprising the steps of:

locating an oxygen sensor in contact with said ambient atmosphere, said sensor comprising:

sensing material selected from metal or its oxides and which, when at an elevated temperature and exposed to a gas containing a changing partial pressures of oxygen, is capable of changing from one metal or metal oxide phase to another such oxide phase and vice versa and associated therewith a change in a measurable physical property thereof;

maintaining a temperature gradient across said sensing material whereby said material exists, during active sensing operation, in at least two of said phases defining a boundary line therebetween generally perpendicular to a longitudinal axis of said temperature gradient; and         furnishing an output signal in response to a change in the physical property of said sensing material, said property being measured across a portion or the entire said sensing material which includes, during active sensing operation, at least two of said phases.

2. The method according to claim 1 wherein said physical property is selected from the group consisting of electrical resistance, mass, and optical absorption.

3. The method according to claim 1 wherein said temperature gradient is maintained by heating means comprising an electrically conductive material located in proximate location to said sensing material and being connectable to a power source.

4. The method according to claim 1 for detecting a change of oxygen partial pressure in an ambient atmosphere through a change of electric resistance of said material, wherein said furnishing step comprises employing spaced apart electrical means located on or within said sensing material to measure the electrical resistance of said portion of said sensing material between said electrical means.

5. The method according to claim 1 wherein said physical property is measured across essentially the entire sensing material.

6. The method according to claim 1 wherein said sensing material is a planar layer and said electrical means are generally parallel to or perpendicular to the longitudinal axis of said temperature gradient of the layer.

7. The method according to claim 3 wherein said heating means comprises an electrically conductive material (a) electrically insulated from said sensing material, (b) located in proximate location to said sensing material, (c) and being connected to said power source for maintaining said temperature gradient.

8. The method according to claim 1 wherein said sensing material is a layer deposited on a substrate.

9. The method according to claim 1 wherein said sensing material is selected from a metal, a compound of two or more metals, or oxides thereof.

10. The method according to claim 9 wherein said metal is selected from the group consisting of copper, palladium, indium, ruthenium, and rhodium; 3d transition metals, rare earth elements.

11. The method according to claim 8 wherein said substrate is planar.

12. The method according to claim 1 wherein said sensing material has a density which is at least 60% of theoretical.

13. The method according to claim 12 wherein said sensing material has an average particle diameter less than 10 microns.

14. The method according to claim 1 wherein the maximum difference in temperatures across the sensing material provided by said heating means during sensing operation corresponds to a ratio of the maximum to the minimum partial pressures of oxygen in the ambient during sensing equal to 10.

15. The method according to claim 11 wherein said planar sensing material is generally rectangular in shape.

16. The method according to claim 1 wherein said sensing material is present in two oxide phases defining a boundary line therebetween generally perpendicular to the axis of the temperature gradient of said layer.

17. The method according to claim 16 wherein said phases comprise two oxides of cobalt: $CoO$ and $Co_3O_4$.

18. The method according to claim 1 where said ambient atmosphere is an automotive exhaust gas.

* * * * *